United States Patent [19]
Lappe et al.

[11] Patent Number: 5,091,546
[45] Date of Patent: Feb. 25, 1992

[54] NOVEL RHODIUM RECOVERY

[75] Inventors: Peter Lappe, Dinslaken; Helmut Springer, Oberhausen, both of Fed. Rep. of Germany

[73] Assignee: Hoechst Aktiengesellschaft, Fed. Rep. of Germany

[21] Appl. No.: 588,665

[22] Filed: Sep. 26, 1990

[30] Foreign Application Priority Data

Oct. 10, 1989 [DE] Fed. Rep. of Germany ....... 3934824

[51] Int. Cl.$^5$ .............................................. C07F 15/00
[52] U.S. Cl. ........................................ 556/23; 423/22
[58] Field of Search ................... 556/136, 20, 22, 23, 556/13; 423/22

[56] References Cited

U.S. PATENT DOCUMENTS

| | | | |
|---|---|---|---|
| 4,390,473 | 6/1983 | Cooper | 260/429 R |
| 4,625,069 | 11/1986 | Siedle et al. | 556/23 X |
| 4,743,699 | 5/1988 | Page et al. | 556/23 |
| 4,987,242 | 1/1991 | Khanna et al. | 556/23 |

FOREIGN PATENT DOCUMENTS

| | | |
|---|---|---|
| 210017 | 1/1987 | European Pat. Off. . |
| 255673 | 7/1987 | European Pat. Off. . |
| 322661 | 12/1988 | European Pat. Off. . |
| 348833 | 1/1990 | European Pat. Off. . |

*Primary Examiner*—Arthur C. Prescott
*Attorney, Agent, or Firm*—Jordan B. Bierman

[57] ABSTRACT

A process for the recovery of rhodium from distillation residues of crude products from the oxo synthesis with rhodium complexed with an organic phosphorous III compound comprising treating the said distillation residues with oxygen or an oxygen containing gas in the presence of an alkali metal salt of a monocarboxylic acid of 2 to 5 carbon atoms at 60° to 120° C. at atmospheric or elevated pressure to form a water-soluble rhodium compound and extracting the mixture with water to obtain an aqueous phase containing the water soluble rhodium compound in a very simple manner without any substantial loss of rhodium.

14 Claims, No Drawings

NOVEL RHODIUM RECOVERY

STATE OF THE ART

The preparation of aldehydes and alcohols by the addition reaction of carbon monoxide and hydrogen with olefinic double bonds (hydroformylation) is known. The reaction is catalyzed by metals of subgroup 8 of the periodic table or compounds thereof which under the reaction conditions form carbonyls or hydrocarbonyls. While in the past almost exclusively cobalt and cobalt compounds were used as catalysts, today rhodium catalysts are used increasingly, although rhodium is much more expensive than cobalt. Rhodium is used in this process by itself or in combination with complexing agents, for example organic phosphines. While the oxo synthesis using rhodium as catalyst requires reaction pressures of 25 to 30 MPa, pressures of 1 to 5 MPa are sufficient if rhodium complex compounds are used.

Rhodium catalysts lead in many cases to significant advantages. They have higher activity and selectivity and moreover allow, in many respects, problem-free operation of the production plant, especially in regard to the implementation of the synthesis and the removal of the products from the reactor. Finally, the classic oxo process based on cobalt catalysts can be in many cases switched over to rhodium catalysts at low investment costs by using the apparatuses already in existence.

However, the separation and recovery of the rhodium without or at least almost without any losses presents great difficulties, irrespective of whether it is used as catalyst with or without an additional complexing agent. After the reaction is completed, the rhodium is present as a carbonyl compound which may further contain ligands dissolved in the hydroformylation product.

To work up the crude oxo product, the pressure is usually reduced in several steps by first reducing the synthesis pressure which, depending on the type of rhodium catalyst used, is about 1 to 30 MPa to about 0.5 to 2.5 MPa. This releases any synthesis gas dissolved in the crude product. The pressure can then be reduced to atmospheric pressure. The rhodium is separated off either directly from the crude product or from the residue of the crude product by distillation. The first method is chosen if, in the preceding hydroformylation stage, rhodium had been used as catalyst without any addition of complexing agent. The second variation is used if the rhodium catalyst contains, apart from carbon monoxide, still further ligands, for example phosphines or phosphites bound in the form of a complex. It can also be utilized in the case where, although the hydroformylation had been carried out with rhodium by itself, a complexing agent had been added to the crude product for stabilizing the rhodium after the pressure release.

A basic fact to keep in mind is that the noble metal is present in the crude product in a concentration of only a few ppm which means that its separation must be carried out with great care. Additional difficulties can arise from the fact that some of the rhodium, particularly if it was used without a ligand, is converted into its metallic form or forms multinuclear carbonyls during the pressure release. This leads to the formation of a heterogenous system consisting of the liquid organic phase and the solid phase which contains rhodium or rhodium compounds.

The recovery of rhodium from the products of the oxo synthesis, including the residues of crude oxo products, has been investigated many times. This work led to the development of a large number of processes, some of which have also found application on an industrial scale. U.S. Pat. No. 4,400,547 relates to the hydroformylation of olefins containing 2 to 20 carbon atoms in the presence of unmodified rhodium as catalyst. After the reaction is complete, a complexing compound such as triphenylphosphine is added to the crude oxo product, and the aldehyde is distilled off. The distillation residue is then treated with oxygen to eliminate the ligand from the complex compound and to recover the rhodium in its active form. Separation of the rhodium and the distillation residue is not possible by this method.

The separation of noble metals such as rhodium from high-boiling hydroformylation residues is also described in U.S. Pat. No. 3,547,964. For this purpose, the residues are treated in the presence of acids such as formic acid, nitric acid or sulfuric acid with hydrogen peroxide. However, due to the high price of hydrogen peroxide and its difficult handling, the industrial application of the process is limited.

According to DE 2,448,005 C2, a distillation residue containing rhodium is first treated with acids and peroxides. Excess peroxides are then destroyed by heating, and the aqueous solution containing the metal catalyst is then reacted in the presence of a water-soluble organic solvent with hydrohalic acid or alkali metal halides and with tertiary phosphines and carbon monoxide or compounds releasing carbon monoxide. Again, this method requires the use of peroxides which have the disadvantages described above and the use of halogen-resistant material.

Finally, in U.S. Pat. No. 4,390,473, a process for the recovery of rhodium and cobalt from a solution which had been used as catalyst in a low-pressure oxo process is described. To separate the metals which are bound in the form of a complex, aqueous formic acid is added to the solution, and an oxgen-containing gas is passed through the solution. This leads to the formation of two phases, one organic and one aqueous, which contain the metals dissolved in the form of formates. After the phases are separated, cobalt and rhodium can be recovered from the aqueous solution. However, the fact that formic acid acts as a reducing agent was found to be a considerable disadvantage in industrial practice. This property had the effect that some of the rhodium was deposited in metallic form during the course of the process and could no longer be recovered.

OBJECTS OF THE INVENTION

It is an object of the invention to develop a process which avoids the disadvantages mentioned above and ensures recovery of the noble metal in a very simple manner without losses or at least almost without losses.

This and other objects and advantages of the invention will become obvious from the following detailed description.

THE INVENTION

The process of the invention for the recovery of rhodium from distillation residues of crude products from the oxo synthesis with rhodium complexed with an organic phosphorous III compound comprises treating the said distillation residues with oxygen or an oxygen containing gas in the presence of an alkali metal salt of a monocarboxylic acid of 2 to 5 carbon atoms at 60° to 120° C. at atmospheric or elevated pressure to form a water-soluble rhodium compound and extracting the mixture with water to obtain an aqueous phase containing the water soluble rhodium compound.

The procedure of the invention does not require any complicated apparatus or the use of expensive chemicals. Nevertheless, it surprisingly leads to the recovery of far more than 90% of the rhodium used and the metal is obtained in a form which allows it to be used again as catalyst without any special additional measures.

The new process starts with the residues of the hydroformylation of olefinic unsaturated compounds which remain at the bottom of the distillation apparatus as a by-product of the alcohols formed after the aldehydes have been distilled off. The residues mainly consist of compounds of higher molecular weight which have been formed from the aldehydes by aldol condensation and can also eliminate water in a subsequent reaction with the formation of unsaturated compounds. The nature of the compounds which have been hydroformylated is unimportant for the claimed procedure. Accordingly, not only residues formed in the reaction of olefins with carbon monoxide and hydrogen but also products of higher molecular weight formed in the reaction of olefinically unsaturated compounds and containing other functional groups in the molecule, apart from the double bond, can be used. However, the central aspect of the new process is the recovery of rhodium from the residues of the hydroformylation of olefins having 2 to 12 carbon atoms, in accordance with the economic importance of the aldehydes prepared from them.

In addition to the saturated and unsaturated condensation products, the residues can additionally also contain compounds which react with the rhodium ions with the formation of complexes and are mostly present in excess compared with rhodium. These compounds include organic phosphorous (III) compounds, particularly phosphines and phosphites and preferably the aryl compounds such as triphenylphosphine and triphenyl phosphite. Their function is to improve the selectivity of the reaction through the formation of stable complex compounds during the reaction and to prevent the precipitation of metallic rhodium after the reaction. In the reaction mixture, the ratio of ligand and rhodium is preferably 2 to 150 and particularly 5 to 50 mol/g-atom of rhodium. As a result of their low volatility, both components are also present in the distillation residue in about the same ratio, the rhodium concentration being between 30 and 1000 ppm, preferably 100 to 500 ppm.

According to the invention, the distillation residue is treated with oxygen and the oxidizing agent is used in pure form or as an oxygen-containing gas mixture, particularly air. The amount of oxygen can be varied within wide limits. It preferably depends on the concentration of the phosphorous (III) compounds in the residue and it is recommended to use 100 to 2000, particularly 300 to 1200, moles of oxygen per mole of phosphorous (III) compound.

According to the invention, the treatment of the distillation residue with oxygen is carried out in the presence of a saturated, straight-chain or branched monocarboxylic acid of 2 to 5 carbon atoms. Examples of suitable acids are acetic acid, propionic acid, n-butyric acid, i-butyric acid and n-valeric acid. Particularly, acetic acid and propionic acid have been proven suitable and they are used in the commercially available form and in such an amount that about 10 to 150, preferably 10 to 50 moles, are present per g-atom of rhodium. The acid is added to the residue before the reaction with oxygen, irrespective of the fact that due to small amounts of aldehyde present in the residue, acid can be formed from the residue itself in the course of the reaction. The exact mode of action of the acid is not known but various observations show that it acts as an initiator, i.e. that it has a decisive effect on the start of the reaction.

An additional very important aspect of the process of the invention is the presence of an alkali metal carboxylate in the residue during the introduction of oxygen into the mixture of the high-boiling compounds. Nor can its role in the course of the reaction be explained with certainty. However, it has been shown that the addition of carboxylate results in a significant increase in the amount of rhodium recovered, i.e., in a further reduction of the rhodium which remains dissolved in the organic phase.

In the context of the new process, salts of saturated, straight-chain or branched mono-carboxylic acids of 2 to 5 carbon atoms are used as alkali metal carboxylates. The sodium and potassium salts of acetic acid, propionic acid, n- and isobutyric acid and n-valeric acid have proven especially suitable. They are used in an amount of 50 to 250, preferably 100 to 180 moles per g-atom of rhodium. The commercially available salts are suitable, although they only go into solution gradually during the course of the oxidation. It is therefore more advantageous to add free acid and the equivalent amount of alkali metal hydroxide to the residue which are immediately dissolved homogeneously and thus become fully effective.

The reaction of the residue with oxygen is carried out at 60 to 120, preferably 80° to 100° C. It can be carried out in the absence of pressure or under pressure, pressures between 0.2 and 1.0 MPa having proven suitable.

In a preferred embodiment of the process of the invention, the residues to be treated with oxygen contain rhodium in a concentration of about 100 ppm and less, preferably 30 to 90 ppm. The reason is that the residual rhodium amounts in the residue treated, according to the invention turned out to be particularly low if the metal concentration in the original solution is within the ranges mentioned. It is therefore recommended to dilute solutions in which the rhodium concentration is more than about 100 ppm. Suitable diluents are particularly higher-boiling aliphatic or aromatic hydrocarbons or hydrocarbon mixtures such as toluene and xylene or also distillation residues freed of the rhodium catalyst.

The reaction time is dependent on the rhodium and ligand concentration in the distillation residue. Furthermore, it is determined by the amount of oxygen used, the reaction temperature and pressure. High concentrations of the dissolved substances require longer treatment times than low concentrations. A large supply of oxygen and elevated pressure shorten the reaction time as does thorough mixing of the residue with oxygen. Temperatures in the lower and upper range of the claimed interval are somewhat less effective than in the middle temperature range.

The reaction of the distillation residue can be carried out continuously or batchwise in conventional apparatures. The oxygen or the oxygen-containing gas is introduced into the reactor via distribution means, and the uniform mixing of the liquid and gaseous phase is, if necessary, aided by stirring.

After the treatment with oxygen has been completed, the organic phase is extracted with water. This is done at room temperature in one step, or more preferably in several steps. The amount of water used depends on the distribution equilibrium of the substance to be extracted between the organic and aqueous phase and the desired rhodium concentration in the aqueous phase. The aqueous solution of the rhodium compound can also be used repeatedly for the extraction via recycling, to concentrate the metal in the solution. The aqueous solution can be used directly for the preparation of the catalyst without any additional purification steps.

In the following examples, there are described several preferred embodiments to illustrate the invention. However, it should be understood that the invention is not intended to be limited to these embodiments.

of the autoclave was and passed into a flask equipped with a cooler.

After the reaction was completed, the autoclave contents were cooled to 60° C. over about 15 minutes, and the addition of air was discontinued. The pressure was then released, 200.0 g of water were added to the reaction mixture, and stirring at 50° to 60° C. was continued for another 15 minutes. The product was removed from the reactor, the phases were separated, and the organic phase was extracted twice with 200.0 g of water each. After the treatment, 1.9 mg of Rh still remained in the organic phase which corresponds to 4.4% of the Rh content of the starting material.

EXAMPLES 2 TO 19

The experimental procedure was analogous to Example 1 and the starting materials, reaction conditions and results are listed in Table 2.

| Example No. | Starting material Type | Amount (g) | Xylene (g) | Temp. (°C.) | t (h) | p (MPa) | N carboxylate Type | Amount (mol/g-atom Rh) | Carboxylic acid Type | Amount (mol/g-atom Rh) | Amount of air (1/h mmol P (III)$^{-1}$) | Rh content in the org. phase (% rel. to starting material) |
|---|---|---|---|---|---|---|---|---|---|---|---|---|
| 2  | B | 400 | 200 | 80 | 5 | 0.25 | $C_3$   | 150 | $C_3$   | 50 | 14 | 5.6 |
| 3  | B | 300 | 300 | 80 | 5 | 0.25 | $C_3$   | 150 | $C_3$   | 50 | 14 | 4.1 |
| 4  | B | 240 | 360 | 80 | 5 | 0.25 | $C_3$   | 150 | $C_3$   | 50 | 14 | 4.1 |
| 5  | A | 360 | 240 | 80 | 5 | 0.25 | $C_2$   | 150 | $C_2$   | 20 | 17 | 4.7 |
| 6  | A | 360 | 240 | 80 | 5 | 0.25 | $C_3$   | 150 | $C_3$   | 20 | 17 | 4.3 |
| 7  | A | 360 | 240 | 80 | 5 | 0.25 | i-$C_4$ | 150 | i-$C_4$ | 20 | 17 | 5.2 |
| 8  | D | 175 | 425 | 80 | 5 | 0.25 | $C_3$   | 150 | $C_3$   | 20 | 70 | 8.0 |
| 9  | D | 175 | 425 | 85 | 5 | 0.25 | $C_3$   | 150 | $C_3$   | 20 | 70 | 6.9 |
| 10 | D | 175 | 425 | 90 | 5 | 0.25 | $C_3$   | 150 | $C_3$   | 20 | 70 | 8.2 |
| 11 | C | 188 | 412 | 80 | 5 | 0.25 | $C_3$   | 150 | $C_3$   | 20 | 14 | 4.3 |
| 12 | B | 300 | 300 | 80 | 5 | 0.25 | $C_3$   | 150 | $C_3$   | 10 | 14 | 5.0 |
| 13 | B | 300 | 300 | 80 | 5 | 0.25 | $C_3$   | 150 | $C_3$   | 20 | 14 | 4.7 |
| 14 | B | 300 | 300 | 80 | 5 | 0.25 | $C_3$   | 150 | $C_3$   | 50 | 14 | 4.1 |
| 15 | B | 300 | 300 | 80 | 5 | 0.25 | $C_3$   | 50  | $C_3$   | 20 | 14 | 4.3 |
| 16 | B | 300 | 300 | 80 | 5 | 0.25 | $C_3$   | 100 | $C_3$   | 20 | 14 | 4.0 |
| 17 | B | 300 | 300 | 80 | 5 | 0.25 | $C_3$   | 150 | $C_3$   | 20 | 14 | 3.9 |
| 18 | D | 175 | 425 | 80 | 5 | 0.25 | $C_3$   | 150 | $C_3$   | 20 | 25 | 6.9 |
| 19 | D | 175 | 425 | 80 | 5 | 0.25 | $C_3$   | 150 | $C_3$   | 20 | 15 | 7.2 |

In Table 1, the materials used are characterized by their most important numercial values.

TABLE 1

|  | Product A | Product B | Product C | Product D |
|---|---|---|---|---|
| Rh content (ppm) | 117 | 142 | 224 | 226 |
| P (III) (mmol/kg) | 2.5 | 4.8 | 15.0 | 7.7 |
| P total (mmol/kg) | 7.2 | 6.3 | 21.1 | 13.4 |
| CO number (mg of KOH/g) | 247 | 300 | 368 | 351 |
| Density 20° C. (g/cm$^3$) | 0.952 | 0.961 | 0.949 | 0.942 |
| Water (%) | 0.09 | 0.05 | 0.09 | 0.22 |

EXAMPLE 1

300.0 g of distillation residue B, 300.0 g of xylene, 8.22 g of 30% pure sodium hydroxide solution and 5.18 g of 99.5% pure propionic acid were initially introduced into a 1 liter glass autoclave equipped with a heating mantle, and the mixture was heated to 78° C. over a period of 15 minutes with stirring. 20 liters of air per hour were then introduced via an immersion tube over a period of 5 hours and under a pressure 0.2 MPa. The reaction was carried out at a constant internal pressure of 0.25 MPa and a constant temperature of 80° C. The waste gas was released via a needle valve in the lid Various modifications of the process may be made without departing from the spirit or scope thereof and it is to be understood that the invention is intended to be limited only as defined in the appended claims.

What we claim is:

1. A process for the recovery of rhodium from distillation residues of crude products from the oxo synthesis with rhodium complexed with an organic phosphorous III compound comprising treating the said distillation residues with oxygen or an oxygen containing gas in the presence of an alkali metal salt of a monocarboxylic acid of 2 to 5 carbon atoms at 60° to 120° C. at atmospheric or elevated pressure to form a water-soluble rhodium compound and extracting the mixture with water to obtain an aqueous phase containing the water soluble rhodium compound.

2. The process of claim 1 wherein air is used as the oxygen-containing gas.

3. The process of claim 1 wherein 100 to 2000 moles of oxygen are used per mole of phosphorous (III) compound.

4. The process of claim 3 wherein 300 to 1200 moles of oxygen are used.

5. The process of claim 1 wherein the monocarboxylic acid is selected from the group consisting of acetic acid, propionic acid, n-butyric acid, i-butyric acid and n-valeric acid.

6. The process of claim 1 wherein 10 to 150 moles of monocarboxylic acid are added to the residues per g-atom of rhodium.

7. The process of claim 6 wherein 10 to 50 moles of acid are added.

8. The process of claim 1 wherein a sodium or potassium salt of acetic acid, propionic acid, n-butyric acid, i-butyric acid or n-valeric acid is added to the residue.

9. The process of claim 1 wherein 50 to 250 moles of an alkali metal salt of monocarboxylic acid of 2 to 5 carbon atoms are added to the residue per g-atom of rhodium.

10. The process of claim 9 wherein 100 to 180 moles of the alkali metal salt are added.

11. The process of claim 1 wherein the treatment of the residue with oxygen or an oxygen-containing gas is carried out at 80° to 100° C.

12. The process of claim 1 wherein the treatment of the residue with oxygen or an oxygen-containing gas is carried out at pressures of 0.2 to 1.0 MPa.

13. The process of claim 1 wherein the rhodium concentration in the residue is up to about 100 ppm.

14. The process of claim 13 wherein the rhodium concentration is 30 to 90 ppm.

* * * * *